United States Patent
Al-Saleh et al.

(10) Patent No.: US 11,448,635 B2
(45) Date of Patent: Sep. 20, 2022

(54) METHOD FOR SCREENING EOR AGENTS EFFECTS ON RESERVOIR ROCK WETTABILITY: AN IN-SITU CONTACT ANGLE MEASUREMENT

(71) Applicant: SAUDI ARABIAN OIL COMPANY, Dhahran (SA)

(72) Inventors: Salah Hamad Al-Saleh, Dhahran (SA); Ahmed Gmira, Dhahran (SA); Ali Abdullah Al-Yousef, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 44 days.

(21) Appl. No.: 16/892,644

(22) Filed: Jun. 4, 2020

(65) Prior Publication Data
US 2021/0382029 A1    Dec. 9, 2021

(51) Int. Cl.
*G01N 33/24* (2006.01)
*G01N 13/02* (2006.01)
*G01N 30/02* (2006.01)

(52) U.S. Cl.
CPC ........... *G01N 33/241* (2013.01); *G01N 13/02* (2013.01); *G01N 30/02* (2013.01); *G01N 2013/0208* (2013.01)

(58) Field of Classification Search
CPC ...... G01N 13/02; G01N 30/02; G01N 33/241; G01N 2013/0208
See application file for complete search history.

(56) References Cited

U.S. PATENT DOCUMENTS

| | | | |
|---|---|---|---|
| 3,643,738 A | 2/1972 | Dreher et al. | |
| 4,688,938 A | 8/1987 | Demoulin et al. | |
| 5,861,946 A | 1/1999 | Hudson et al. | |
| 8,474,306 B1 | 7/2013 | Behroozi | |
| 8,768,628 B2 | 7/2014 | Ghedan et al. | |
| 9,016,111 B2 | 4/2015 | Stukan et al. | |
| 10,139,347 B2 | 11/2018 | Washburn | |
| 10,794,812 B2 * | 10/2020 | Gmira | G01N 13/02 |

(Continued)

FOREIGN PATENT DOCUMENTS

BR  102015011187 A2   5/2017
CN  102322247 A   1/2012
(Continued)

OTHER PUBLICATIONS

Mahani et al. "Kinetics of the Low Salinity Waterflooding Effect Studied in a Model System," SPE 165255 (Year: 2013).*
(Continued)

*Primary Examiner* — John Fitzgerald
(74) *Attorney, Agent, or Firm* — Osha Bergman Watanabe & Burton LLP

(57) ABSTRACT

A method for determining a contact angle of a hydrocarbon on a rock surface, the method including injecting a first brine fluid into a test cell, the first brine fluid having an initial ionic composition, injecting a hydrocarbon fluid into the test cell, contacting the hydrocarbon fluid with the first brine fluid, forming a droplet, measuring the contact angle of the hydrocarbon fluid, at least partially displacing the first brine fluid with an inert gas, measuring a ionic composition of the displaced first brine fluid in an ionic chromatograph, and comparing the measured ionic composition to the initial ionic composition.

7 Claims, 5 Drawing Sheets

(56) References Cited

U.S. PATENT DOCUMENTS

| | | | |
|---|---|---|---|
| 10,908,063 B2* | 2/2021 | Gmira | G01N 13/02 |
| 2015/0233223 A1 | 8/2015 | AlAmeri et al. | |
| 2016/0177171 A1* | 6/2016 | Hern Ndez Al Tamirano | C09K 8/52 166/268 |
| 2019/0094120 A1 | 3/2019 | Gmira et al. | |

FOREIGN PATENT DOCUMENTS

| | | |
|---|---|---|
| CN | 105043936 A | 11/2015 |
| CN | 109470603 A | 3/2019 |
| CN | 110108599 A | 8/2019 |
| JP | 2017003337 A | 1/2017 |
| KR | 20160128554 A | 11/2016 |

OTHER PUBLICATIONS

International Search Report and Written Opinion issued in corresponding International Patent Application No. PCT/US2020/048905, dated Mar. 10, 2021 (17 pages).

Lamour, Guillaume et al., "Contact Angle Measurements Using a Simplified Experimental Setup", In the Laboratory, Journal of Chemical Education, American Chemical Society and Division of Chemical Education, Inc., vol. 87, No. 12, Dec. 2010, pp. 1403-1407 (5 pages).

Rao, D.N., "Correlation of Oil-Water Flow Behaviour in Reservoir Rocks With Dynamic Contact Angles", Journal of Canadian Petroleum Technology, vol. 41, No. 7, Jul. 2002, pp. 31-38 (8 pages).

Shedid, Shedid A. and Mamdouh T. Ghannam, "Factors affecting contact-angle measurement of reservoir racks", Journal of Petroleum Science and Engineering, Elsevier B.V., 44, Nov. 2004, pp. 193-203 (11 pages).

Yousef, Ali A. et al., "The Impact of the Injection Water Chemistry on Oil Recovery from Carbonate Reservoirs", SPE 154077, Society of Petroleum Engineers, Apr. 2012 (14 pages).

Yuan, Yuehua and T. Randall Lee, "Chapter 1: Contact Angle and Wetting Properties", Surface Science Tecniques, Springer Series in Surgace Sciences 51, Editors G. Bracco and B. Holst, Springer-Verlag Berlin Heidelberg, 2013, pp. 3-34 (32 pages).

* cited by examiner

METHOD FOR SCREENING EOR AGENTS EFFECTS ON RESERVOIR ROCK WETTABILITY: AN IN-SITU CONTACT ANGLE MEASUREMENT

BACKGROUND

Water flooding with brine or seawater composition is often used for secondary recovery processes in hydrocarbon-bearing reservoirs. Enhancing oil recovery in naturally fractured reservoirs by injecting a chemistry-optimized water has been widely investigated and gained increasing interest in the last decade. This interest is mainly driven by the attractive economics of such technology because of the existing water flooding facilities. Numerous multi-scale research efforts were initiated in order to capture the impact of modified injected water composition on reservoir rocks wettability and the increase of reservoirs oil recovery.

Rock/fluid interface behavior is an important parameter in the understanding of the effect of the injected brine ionic composition. The contact angle between a hydrocarbon and a rock is a physical measurement, much needed in the oil industry in general and enhanced oil recovery, in particular. The measurement of the contact angle between hydrocarbon and rock is mainly used to assess the effect of injected brine composition, additives (surfactant, polymers, alkali . . . ) and also the activity of the interface at defined temperature and pressure.

Contact angle measurement of hydrocarbon, for example, is based on an optical method. A hydrocarbon drop with vertical symmetry is generated from a vertical needle, placed on a rock surface. The hydrocarbon drop shape results from a balance between gravity forces, buoyancy, pressure caused by the curvature interface and interfacial tension forces. Contact angle is then calculated from the hydrocarbon drop using the Laplace equation.

The above process requires extensive cleaning to avoid contamination, which is also time consuming when it comes to testing multiple brines with different compositions, additives, and temperature and pressure conditions.

The prior art describes contact angle measurements by using a static method that requires multiplication of single runs. Screening the effect of additives and fluids compositions is usually performed by completing a measurement for one set of fluids followed by a drainage, a thorough cleaning, injection and then measurement for the following set of fluids.

The current practices are based on measuring contact angle of hydrocarbon on separate single runs. This method requires intensive cleaning, time and is a source of experimental fluctuations. This will add uncertainties associated with each individual run and will not emulate the real contact angle changes occurring at the interfaces of brines with additives and/or modified ionic composition.

SUMMARY

In one aspect, embodiments disclosed herein relate to a method for determining contact angle of a hydrocarbon on a rock surface in a brine fluid. The method may include injecting a first brine fluid into a test cell, the first brine fluid having an initial ionic composition, injecting a hydrocarbon fluid into the test cell, contacting the hydrocarbon fluid with the rock surface, forming a droplet, measuring the contact angle of the hydrocarbon fluid, at least partially displacing the first brine fluid with an inert gas, measuring a ionic composition of the displaced first brine fluid in an ionic chromatograph; and comparing the measured ionic composition to the initial ionic composition.

In another aspect, embodiments disclosed herein relate to a method for determining contact angle of a hydrocarbon on a rock surface in a brine fluid. The method may include injecting a first brine fluid into a test cell, the first brine fluid having an initial ionic composition, injecting a hydrocarbon fluid into the test cell, contacting the hydrocarbon fluid with the first brine fluid, forming a droplet, measuring the contact angle of the hydrocarbon fluid in contact with the rock surface, at least partially displacing the first brine fluid with an inert gas, measuring a ionic composition of the displaced first brine fluid in an ionic chromatograph, and comparing the measured ionic composition to a second initial ionic composition of a second brine fluid.

In another aspect, embodiments disclosed herein relate to a system useful for determining contact angle of a hydrocarbon on a rock surface in a brine fluid. The system may include a test cell configured to enclose a hydrocarbon fluid disposed on a rock surface in a first brine fluid, a first brine fluid tank configured to hold a volume of the first brine fluid, the first brine fluid having an initial ionic composition, a second brine fluid tank configured to hold a volume of a second brine fluid, the second brine fluid having a second initial ionic composition, at least one pump fluidly coupled to the test cell and the first and second brine fluid tanks, and a control system communicably coupled to the pump.

In another aspect, embodiments disclosed herein relate to a process for determining contact angle of a hydrocarbon fluid on a rock surface in a brine fluid. The process may be performed in a system including a first pump (126) fluidly connected via a valve V0 to a first brine fluid tank (120a) holding a volume of a first brine fluid and via a valve V2 to a second brine fluid tank (120b) holding a volume of a second brine fluid, a second pump (125) fluidly connected via a valve V11 and a valve V12 to an inert gas tank (116) holding a volume of inert gas and via the valve V11 and a valve V13 a hydrocarbon tank (115) holding a volume of hydrocarbon fluid, and a test cell (105) configured to measure the contact angle of the hydrocarbon fluid. The test cell may be fluidly connected via a valve V4 and valves V7, V8, and V10 to the first brine fluid tank, via a valve V5 and the valves V7, V8, and V10 to the second brine fluid tank, via a valve V14 to the inert gas tank, and via a valve V15 and a valve V19 to the hydrocarbon fluid tank. The process may include opening valves V0, V1, V4, V7, V8, and V10, injecting the first brine from the first brine tank using the first pump, filling the test cell with the first brine fluid, heating the test cell with a heating coil, stopping injecting the first brine fluid when a pressure and a temperature of the test cell have reached reservoir conditions, and closing valves V0, V1, V4, V7, V8, and V10, opening valves V11, V13, V15, and V19, injecting the hydrocarbon fluid from the hydrocarbon fluid tank into the test cell using the second pump, closing the valves V11, V13, V15, and V19, stopping injecting the hydrocarbon fluid, and measuring the contact angle of the hydrocarbon droplet on the rock surface in the brine fluid.

Other aspects and advantages will be apparent from the following description and the appended claims.

DETAILED DESCRIPTION

Figure 1:
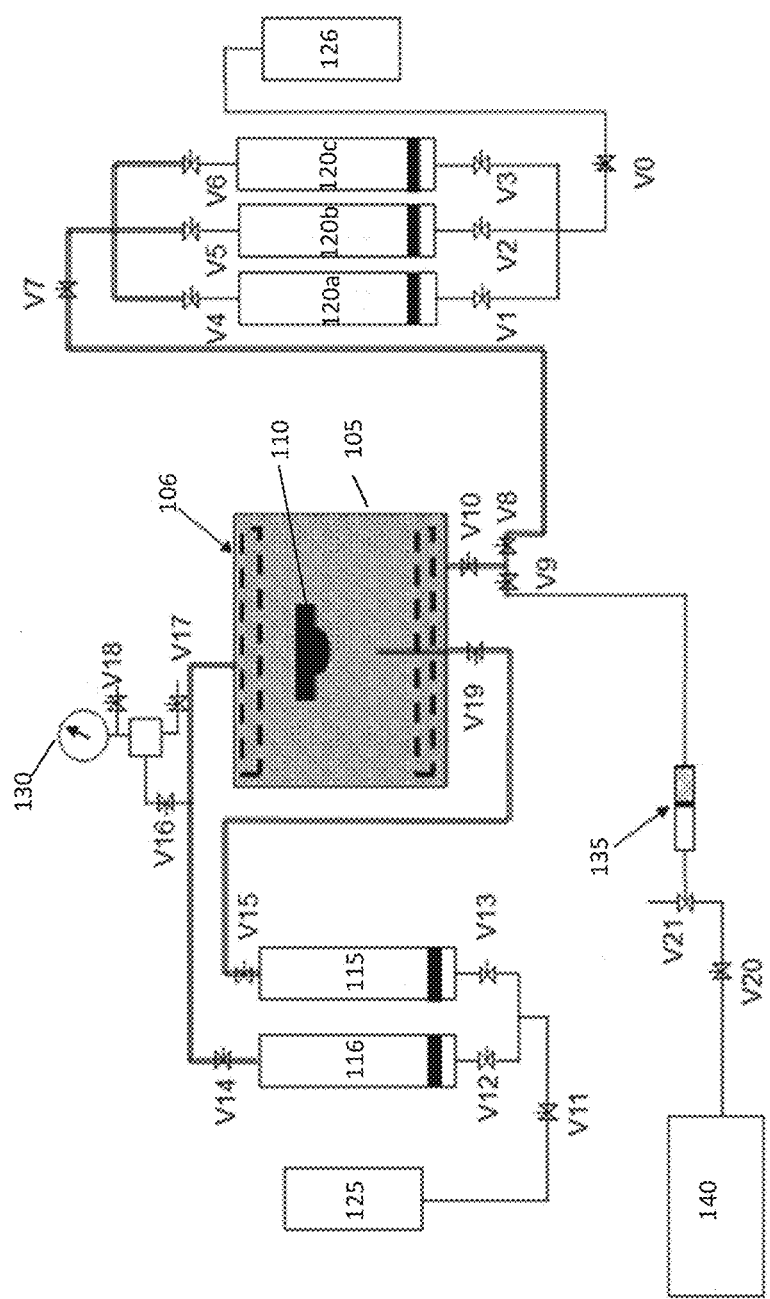
FIG. 1 is a schematic illustration of an example implementation of the system according to one or more embodiments disclosed herein.

Embodiments disclosed herein relate methods and systems for improving contact angle measurement by using an inert gas, such as nitrogen, to displace and replace brine fluids inside a high pressure high temperature (HPHT) chamber at experimental conditions. The sequential replacement is completed when the ionic composition of the drained fluid matches the initial injected fluid. This may ensure a consistent screening for wettability alteration modifiers and an optimized experimental protocol. As used herein, "match" can refer to equivalent compositions and compositions that are substantially the same, such as a drained fluid having an ionic composition that is more than 90% that of the initial injected fluid, an ionic composition that is more than 95% that of the initial injected fluid, an ionic composition that is more than 98% that of the initial injected fluid, or an ionic composition that is more than 99% that of the initial injected fluid.

The present disclosure describes implementations of systems and method for determining contact angle. In some aspects, such implementations include an in-situ dynamic measurement method to determine an ionic composition gradient effect and/or any EOR agents on a droplet of a hydrocarbon fluid. Example implementations include a test cell that is used for measurements at various conditions (for example, at standard conditions, high temperature/high pressure conditions, or both). In some aspects, in-situ brine liquids may be circulated to the test cell to assess an impact of an ionic composition gradient and/or EOR agents on oil recovery. In some aspects, the circulation of multiple brines (for example, serially) may be controlled by measuring a parameter of the brines (for example, by using ionic chromatography) and using the measurement to control brine replacements inside the test cell. In some aspects, such implementations may enable a realistic measurement of contact angle caused by an ionic composition gradient and/or any EOR agents and various determining parameters (for example, crude oil composition, reservoir pressure and temperature, and other parameters). One such example of an ionic composition of the hydrocarbon fluid disclosed herein is the salinity of the hydrocarbon fluid. The salinity of the hydrocarbon fluid may change depending on the brine fluid used for testing.

Accordingly, a new experimental method to measure in-situ contact angle between hydrocarbon fluid and a reservoir rock at reservoir conditions of different compositions injected successively is disclosed herein. The method may be buffered by an inert gas, such as nitrogen. Contact angle of a first brine fluid may be measured and then nitrogen gas may be injected gradually inside the cell to purge the first brine fluid. The drained brine fluid may then be diverted to an in-line ionic chromatography analyzer (IC) to determine the ionic composition. Nitrogen gas injection may stop as soon as the first brine fluid is completely drained. A second brine fluid may then be gradually introduced to the cell while maintaining temperature and pressure conditions. A third, fourth, fifth, etc. brine fluid may also be introduced in this fashion (inert gas displacement followed by brine fluid injection). This approach may provide a contamination-free, time efficient process in measuring contact angle between hydrocarbon fluid and a reservoir rock.

The contact angle between a liquid and rock, is a physical magnitude that is much used in various scientific and technical fields. It represents the energy brought into play by the forces of intermolecular cohesion on an interface between a liquid and a surface. Contact angle is expressed in terms of degrees.

Calculating the value of the contact angle between a liquid and a surface is generally known, and operates on the basis of optical measurements of the shape and dimensions of a drop of liquid hydrocarbon deposited on the rock. The drop takes a shape that results from the equilibrium among the forces of gravity, buoyancy, the forces of interfacial tension, adhesion, and the pressure due to the curvature of the interface.

By analyzing the shape and dimensions of the drop, it is possible to determine the value of the contact angle in an absolute way.

Turning now to the figures, FIG. 1 is a schematic illustration of one embodiment of the contact angle measurement system 100. As shown, the system 100 includes a test cell 105 that encloses a rock surface 110. In some aspects, the liquid hydrocarbon drop deposited on the rock surface 110 is a crude oil sample (or other hydrocarbon liquid sample).

The test cell 105, in some aspects, may be a contact angle goniometer that is operable (for example, through imaging devices and a microprocessor based software system) to measure a static contact angle, as well as advancing and receding contact angles, between the hydrocarbon fluid sample and the rock. In some aspects, the test cell 105 may be a DSA100, KRUSS Gmbh or IFT-10, Corelab.

Using these devices, different contact angles between hydrocarbon fluid drops and rocks may be measured. For example, a static contact angle, generally, is a measurement of where a liquid-rock interface meets.

The contact angle measurement, in some aspects, may help determine an effectiveness of secondary or tertiary production processes, such as water flooding. For example, water flooding, generally, refers to the process of injecting water (or water-based liquid such as brine) into a reservoir to increase reservoir pressure and thereby increase hydrocarbon production. Thus, the wettability of a reservoir formation and mobility of the hydrocarbon fluid—whether such formation is water-wet or oil-wet—and how water flooding can effect such wettability and hydrocarbon mobility, as determined through contact angle measurement, may affect a choice or operation of stimulation.

The system 100 includes a hydrocarbon fluid sample tank 115 that is fluidly coupled to the test cell 105 though a valve V15 (for example, modulating or shut-off). Although shown as a single tank 115, there may be multiple different tanks 115 fluidly coupled to the test cell 105 through a single or multiple valves V15. Each tank 115 may enclose a similar or different type of hydrocarbon fluid sample (for example, crude oil from different formations).

As illustrated, the system 100 also includes a first brine fluid tank 120a that is fluidly coupled to the test cell 105 through valve V4. A second brine fluid tank 120b is fluidly coupled to the test cell 105 through valve V5. A third brine fluid tank 120c is fluid coupled to the test cell 105 through valve V6. Although shown as three tanks, there may be greater or fewer than three tanks fluidly coupled to the test cell 105 through a single or multiple valves in a similar manner as illustrated. Each tank may enclose a similar or different type of brine (for example, each having a different ionic composition, different conductivity, or other property).

One or more pumps 125 is also fluidly connected to the hydrocarbon fluid sample tank 115. A second pump 126 is also fluidly connected to the brine tanks 120a-c. Both pumps may be operable to circulate the hydrocarbon fluid and brine fluids from the respective tanks 115 and 120a-c. As illustrated, the pump 125 is fluidly connected to the tank (or tanks) 115 through valves V11 and V13, while the pump 126 is also fluidly connected to the tanks 120a-c through valves V0, V1, V2, and V3.

The one or more pumps 125 may also be fluidly connected to an inert gas tank 116 through vales V11 and V12. The inert gas tank 116 may be fluidly connected to the test cell 105 through valve V14. The inert gas held in inert gas tank 116 may be useful for flushing the test cell 105 after an contact angle measurement is performed. The inert gas may be injected into the test cell at reservoir pressure, and heating element 106 may heat the inert gas to reservoir conditions in the test cell 105. Accordingly, the test cell may be kept at reservoir conditions during filling, testing, and purging. Additionally, the flow lines running from brine tanks 120a-120c may be a heated line equipped with an electrical trace, or other similar device, to deliver the brine to the test cell 105 at, or near, reservoir temperature.

Pumps 125 and 126, as well as the tanks 115, 116, and 120a-c may be connected such that the inert gas inlet may be located at the top of the test cell 105, while the liquid inlets for the one or more brines and hydrocarbon fluid may be located at the bottom of test cell 105. Further, the pumps 125 and 126, and the gas flowrate, may be controlled to minimally disturb the liquids. For examples, the pumps may be operated such that the fluids and gases are slowly pushed rather than being rapidly pushed causing a blowout, splashing, mixing, etc.

The volume of inert gas may depend on the test experimental conditions such as temperature, pressure, and brine composition. Injecting of the inert gas may be controlled by pump 125 and the back pressure regulator (BPR) 130. The inert gas injection may continue until the brine is completely drained through valve V9 (i.e., no additional fluids are collected from valve V9), or until after an ionic chromatography test is performed with the excess inert gas being vented by valve V17. BPR 130 may be equipped with one or more valves (V16, V17, and V18) to control the pressure of the inert gas as it is injected into test cell 105, or allow the removal of inert gas when brine is pumped into test cell 105.

As illustrated in FIG. 1, the system 100 also includes a drain system for removing a brine/hydrocarbon sample after contact angle measurement. Valve V10 (for example, modulating or shut-off) may be fluidly coupled to an outlet of the test cell 105 and a filter 135 through valve V9. Once filtered, the brine may be fed through valves V21 and V20 to an ionic chromatography (IC) unit 140. The IC 140 measures the level of dissolved salts, or ionic composition, of the brine that is removed from the test cell 105. By comparing the measured dissolved salts of the drained brine to the known level of dissolved salts in the fresh brine, it may be possible to determine if the test cell 105 has been completely cleaned of residual hydrocarbon.

System 100 also includes a control system (for example, microprocessor based, electromechanical, pneumatic, or other form of control system (not illustrated)). The control system may send commands to, and receive information from, the pumps. For example, the control system may send commands to the pump(s) to start or stop, or slow down or speed up, or both. The pump(s) may send feedback to the control system, such as speed, flow rate, frequency, or a combination. In some aspects, the control system may include or be controllably coupled to a variable frequency drive connected to the pump motor.

The control system may also be communicably coupled to send commands to, and receive information from, the valves V0-V21. For example, the control system may send commands to the valves V0-V21 to open fully or close fully, modulate toward open or modulate toward close. The valves V0-V21 may send feedback to the control system, such as status (open or close), percent open, or a combination.

The control system may also be communicably coupled to send commands to, and receive information from, the test cell 105. For example, the control system may send commands to the test cell 105, such as, to perform contact angle measurement or heat the test cell with heating element 106.

The control system may also be communicably coupled to receive information from the IC 140. For example, the control system may send a signal to the IC 140 to perform the chromatography, and may receive feedback from the IC 140 in the form of a measured ionic composition.

Using the system 100 as illustrated in FIG. 1, the following process steps for successive contact angle measurements may be performed.

The control system may turn on pump 126, open valves V0, V1, V4, V7, V8, and V10. The pump 126 may inject a first brine from brine tank 120a, filling test cell 105 with the first brine fluid. The heated line from the brine tank 120a to the test cell 105, and/or the heating element 106 may heat the brine and the test cell to reservoir conditions, and the pump 126 may provide the pressure to keep the first brine at reservoir pressure. When pressure and temperature have reached reservoir conditions and stabilized, the control system may close valves V10, V8, V7, V4, V1, V0, and stop pump 126. These operations may happen simultaneously, or sequentially in any order.

After the control system closes valves V10, V8, V7, V4, V1, V0, and stops pump 126, the control system may turn on pump 125, open valves V11, V13, V15, and V19 to the hydrocarbon fluid from tank 115 in test cell 105. The control system may then close valves V19, V15, V13, and V11, stop pump 125, and start the cell 105 measuring contact angle versus time of the hydrocarbon droplet on the rock surface.

After the contact angle measurement is performed, the control system may start pump 125, open valves V11, V12, V14, and V16 to inject inert gas from inert gas tank 116 into the test cell 105. The control system may also open valves V10 and V9 to drain the first brine fluid from the test cell 105 to the filter 135. During inert gas injection, the control system may use pressure adjustment valve V18 to maintain a stable reservoir pressure within the test cell 105 during the purge process. Pressure adjustment valve V18 may be at least partially opened to let a portion of the inert gas leave the system, thereby stabilizing the pressure generated by pump 125. Valve V18 may be controlled by the BPR 130 and the control system to maintain the test cell pressure constant during the displacement process. If the vessel pressure is higher than the test pressure, valve V18 will release pressure to maintain the equilibrium. If the vessel pressure is lower than test pressure, V18 will close, causing pump 125 to pressurize the test cell to maintain the equilibrium pressure.

Once the first brine fluid is fully drained from test cell 105, the control system may stop pump 125 and close valves V16, V14, V12, V11, V10, V9 and V20. The drained first brine fluid may be collected and filtered in filter 135. After filtering, the control system may open valve V20 to allow the filtered brine fluid to enter the IC 140 for analysis. The IC 140 will measure the ionic composition of the drained brine fluid and compare the measured ionic composition of the drained brine fluid against a known ionic composition of fresh brine fluid. If the measured ionic composition matches the known ionic composition of the fresh brine fluid, the control system will indicate that the test cell 105 has been completely cleaned. If the measured ionic composition does not match the known ionic composition of the fresh brine fluid, the control system will indicate that the test cell 105 has not been completely cleaned and repeat the above steps to inject the first brine fluid into the test, and then purge the first brine fluid with inert gas, without injecting the hydrocarbon fluid. This process is repeated until measured ionic composition matches the known ionic composition of the fresh brine fluid.

Once the control system has determined that the test cell 105 has been completely cleaned, the control system will begin testing the second brine fluid by starting pump 126 and opening valves V0, V2, V5, V7, V8, and V10 to fill the test cell 105 with the second brine fluid. The steps of injecting the hydrocarbon drop, measuring the contact angle, and draining the test cell may then be repeated. Additionally, the above process may be repeated for the third brine fluid, as illustrated, and may start again with the first brine fluid, or proceed with a fourth, fifth, sixth, etc. brine fluid (not illustrated).

During brine fluid injection into test cell 105, the control system may open valve V16 and vent valve V17 to allow the release of inert gas from the test cell 105. This release of inert gas may maintain the test cell 105 at isobaric conditions. During injection of inert gas and draining of the brine fluid from test cell 105, vent valve V17 may be closed.

Figure 2:
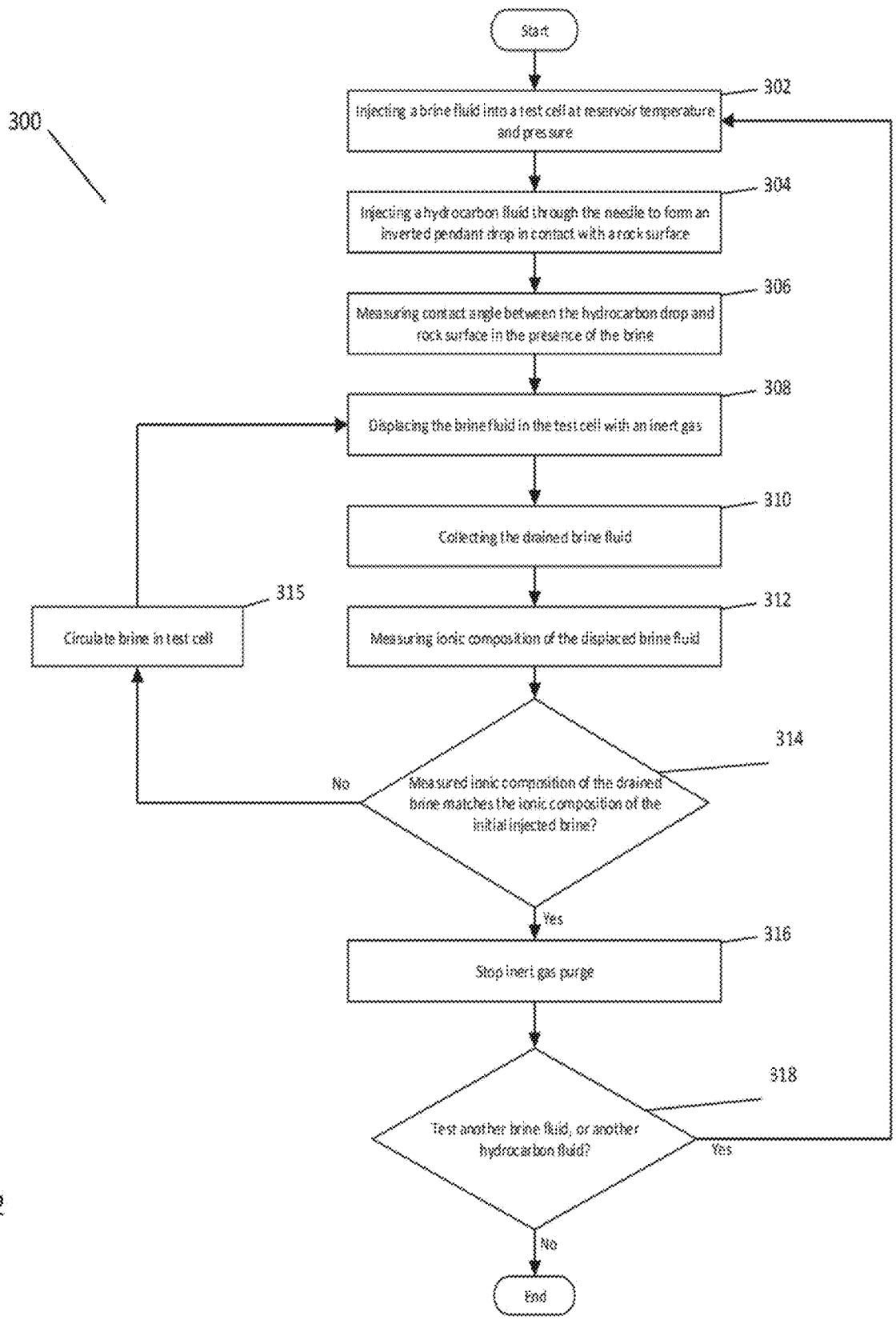
FIG. 2 is a flowchart that illustrates an example method according to one or more embodiments disclosed herein.

FIG. 2 is a flowchart that illustrates an example method 300 for measuring contact angle between the hydrocarbon fluid sample and the rock with the system 100. In some aspects, by determining one or more contact angles between the hydrocarbon fluid sample and the rock using two or more different brine fluids, a wettability may be more accurately and easily determined in a single test set up with the test cell 105. Method 300 may begin at step 302, which includes injecting a brine fluid into the test cell to fill the cell.

Method 300 may continue at step 304, which includes injecting a hydrocarbon fluid to the test cell. Step 306 includes measuring contact angle between the hydrocarbon fluid and the rock surface. Step 308 includes displacing the brine fluid in the test cell with an inert gas. For example, once the contact angle has been measured in step 306, the brine fluid may be drained by injecting inert gas so that the test cell may be cleaned and avoid contaminating the next brine fluid.

Method 300 may continue with step 310, which includes collecting the drained brine fluid. The collected fluid may also be filtered in a filter. Step 312 may include measuring the ionic composition of the drained brine fluid. For example, the ionic chromatography unit may measure ionic composition. Such measured values may be sent to the control system from the IC. The control system may compare the measured values to a known (or measured) value of the same property of the fresh brine fluid.

Method 300 may continue at step 314, which includes a determination of whether the measured property (for example, ionic composition) of the displaced brine fluid matches the known or measured same property of the fresh brine fluid. For instance, when the measured value of the property of the displaced brine fluid matches (or substantially matches, within 1%) the known value of the property of the fresh brine fluid, the method may proceed at step 316 and the control system may stop the flow of inert gas to the test cell 105. If the determination in step 314 does not match the property of the fresh brine fluid, then method 300 continues at step 315, where additional brine fluid is circulated to the test cell, and steps 308, 310, 312, and 314 are repeated until the measured property matches the known fresh property. After the inert gas is stopped in step 316, the method may continue at step 318 and determine if another brine fluid, or another hydrocarbon, is to be tested. If another brine fluid is to be tested, the method may start over at step 302, otherwise the method ends.

Figure 3:
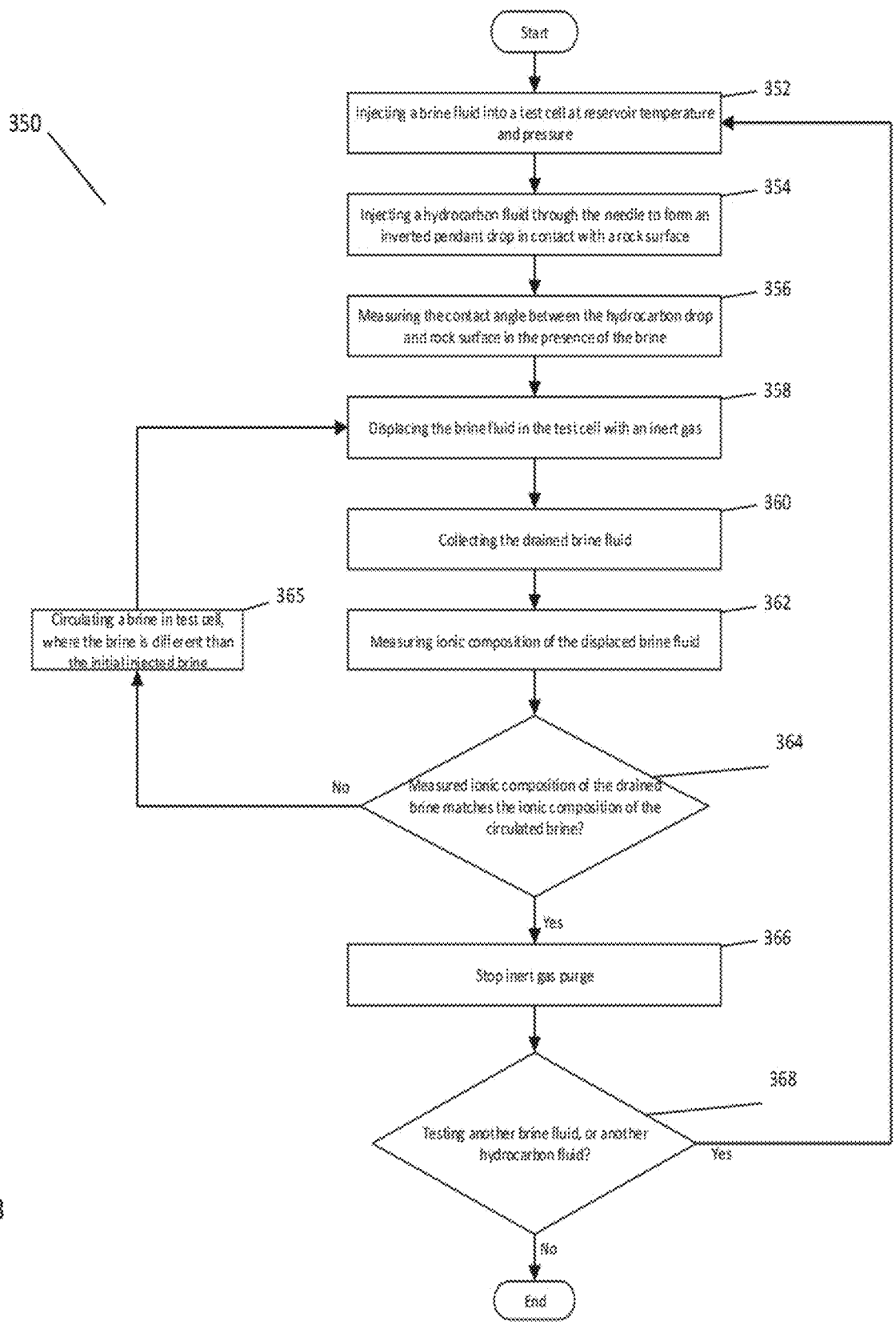
FIG. 3 is a flowchart that illustrates an example method according to one or more embodiments disclosed herein.

FIG. 3 is a flowchart that illustrates an example method 350 for measuring contact angle between the hydrocarbon fluid sample and the brine fluid with the system 100. In some aspects, by determining one or more contact angles between the hydrocarbon fluid sample and a rock surface using two or more different brine fluids, a wettability may be more accurately and easily determined in a single test set up with the test cell 105. Method 350 may begin at step 352, which includes injecting a brine fluid into the test cell to fill the cell.

Method 350 may continue at step 354, which includes injecting a hydrocarbon fluid to the test cell. Step 356 includes measuring contact angle between the hydrocarbon fluid and the brine fluid. Step 358 includes displacing the brine fluid in the test cell with an inert gas. For example, once the contact angle has been measured in step 356, the brine fluid may be drained by injecting inert gas so that the test cell may be cleaned and avoid contaminating the next brine fluid.

Method 350 may continue with step 360, which includes collecting the drained brine fluid. The collected fluid may also be filtered in a filter. Step 362 may include measuring the ionic composition of the drained brine fluid. For example, the ionic chromatography unit may measure ionic composition. Such measured values may be sent to the control system from the IC. The control system may compare the measured values to a known (or measured) value of the same property of the fresh brine fluid.

Method 350 may continue at step 364, which includes a determination of whether the measured property (for example, ionic composition) of the displaced brine fluid matches the known or measured same property of a fresh second brine fluid. For instance, when the measured value of the property of the displaced brine fluid matches (or substantially matches, within 1%) the known value of the property of the fresh second brine fluid, the method may proceed at step 366 and the control system may stop the flow of inert gas to the test cell 105. If the determination in step 364 does not match the property of the fresh second brine fluid, then method 350 continues at step 365, where the second brine fluid is circulated to the test cell, and steps 358, 360, 362, and 364 are repeated until the measured property matches the known fresh property. After the inert gas is stopped in step 366, the method may continue at step 368 and determine if another brine fluid, or another hydrocarbon, is to be tested. If another brine fluid is to be tested, the method may start over at step 352, otherwise the method ends.

Tables 1, 2 and 3 are comparison of ionic composition of the initial and the drained fluids, respectively (seawater, diluted seawater and deionized water).

TABLE 1

Ionic composition of initial and drained seawater

| Ions | Initial Seawater (mg/L) | Drained Seawater (mg/L) |
|---|---|---|
| Calcium | 690 | 702 |
| Chloride | 42077 | 41516 |
| Magnesium | 2027 | 2032 |
| Sodium | 17919 | 18323 |
| Sulfate | 3983 | 4151 |
| TDS | 66696 | 66724 |

TABLE 2

Ionic composition of initial and drained diluted seawater

| Ions | Initial Diluted Seawater (mg/L) | Drained Diluted Seawater (mg/L) |
|---|---|---|
| Calcium | 327 | 339 |
| Chloride | 15544 | 16350 |
| Magnesium | 954 | 975 |
| Sodium | 9371 | 10935 |
| Sulfate | 1965 | 2084 |
| TDS | 28161 | 30683 |

TABLE 3

Ionic composition of initial and drained deionized water

| Ions | Initial Deionized Water (mg/L) | Drained Deionized Water (mg/L) |
|---|---|---|
| Calcium | <10 | <10 |
| Chloride | <5 | <5 |
| Magnesium | <10 | <10 |
| Sodium | <10 | <10 |
| Sulfate | <10 | <10 |
| TDS | — | — |

Once the properties match, the method 350 may continue at step 368, which includes a determination of whether another brine fluid (for example, a second brine fluid, a third brine fluid, a fourth brine fluid, and so on) is to be tested. For example, if multiple (for example, more than two) brine fluids are to be used in tested, then method 350 may continue back at step 352. Otherwise, method 350 may end.

Example

Contact angle measurements on a rock surface in three (3) crude oil/brine fluid systems were performed at 70° C. and 2000 psi. Successive replacement of brine fluid was performed using nitrogen gas to displace each brine fluid at isobaric and isothermal conditions. The following fluids were used:

Brine 1: Seawater;
Brine 2: Diluted seawater;
Brine 3: Deionized water;
Hydrocarbon: Dead crude oil.

Drained brine was collected, filtered, and the ionic composition analyzed and compared with the initial injected brine compositions. This process was repeated with brine 1, 2, and 3.

Figure 4:
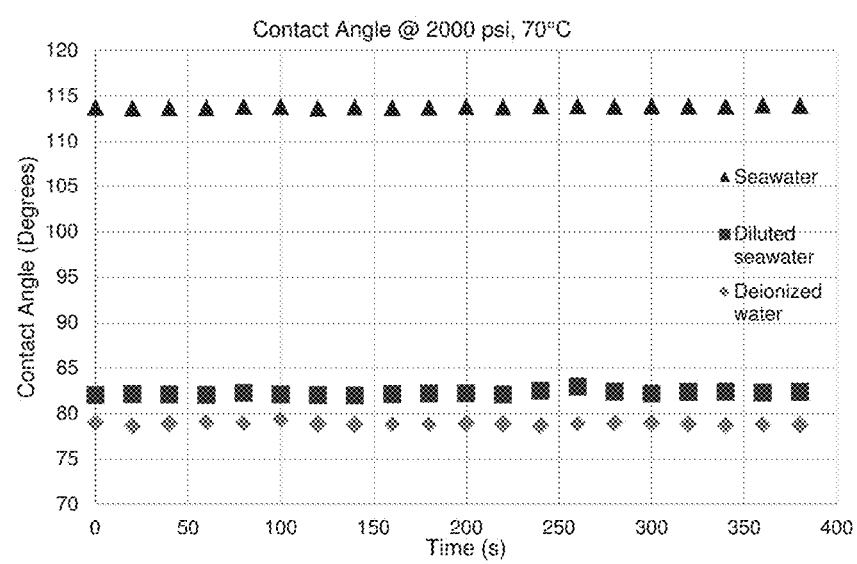
FIG. 4 is an illustration of contact angle measured using the system and method according to one or more embodiments disclosed herein.

FIG. 4 illustrated the contact angle between crude oil and the rock surface in the three different brines (seawater, diluted seawater and deionized water) replaced successively using the proposed method of nitrogen gas buffering. As seen, while contact angle for seawater is high, approximately 114 degrees, deionized water and diluted seawater are low at 79 and 82 degrees, respectively.

Figure 5:
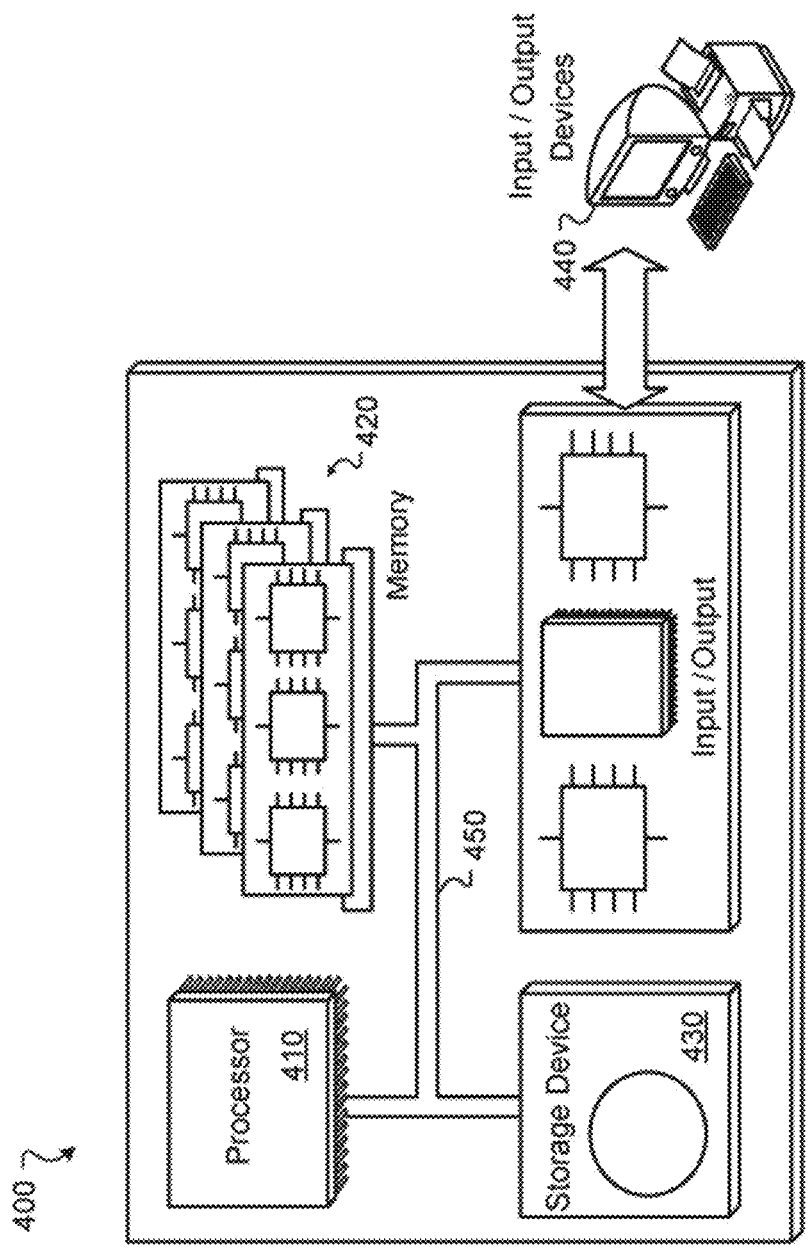
FIG. 5 is a schematic illustration of an example control system according to one or more embodiments disclosed herein.

FIG. 5 is a schematic illustration of an example controller 400 (or control system) for an contact angle measurement system. For example, the controller 400 can be used for the operations described previously, for example as or as part of a control system that performs one or more steps of method 300 described in FIG. 3. For example, the controller 400 may be communicably coupled with, or as a part of, the control system discussed in related to FIG. 1.

The controller 400 may include various forms of digital computers, such as printed circuit boards (PCB), processors, or digital circuitry. Additionally, the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 400 may include a processor 410, a memory 420, a storage device 430, and an input/output device 440. Each of the components 410, 420, 430, and 440 are interconnected using a system bus 450. The processor 410 is capable of processing instructions for execution within the controller 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the controller 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the controller 400. In one implementation, the storage device 430 is a computer-readable medium. In various different implementations, the storage device 430 may be a floppy disk device, a hard disk device, an optical disk device, or a tape device.

The input/output device 440 provides input/output operations for the controller 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of what may be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described should not be understood as requiring such separation in all implementations, and it should be understood that the described program components and systems can generally be integrated together in a single software product or packaged into multiple software products.

Advantageously, the systems and processes described herein may allow for realistic emulation of the effect of brine composition on the contact angle measurement, and realistic emulation of the effect of additives on interfacial phenomena. The systems and methods may eliminate uncertainties due to multiple separated runs and contamination between runs, may be efficient with respect to experimental time management, and may minimize the amount of solvents and chemicals used for cleaning that follows each single run.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A system, comprising:
   a test cell configured to enclose a hydrocarbon fluid disposed on a rock surface in a first brine fluid;
   a first brine fluid tank configured to hold a volume of the first brine fluid, the first brine fluid having an initial ionic composition;
   a second brine fluid tank configured to hold a volume of a second brine fluid, the second brine fluid having a second initial ionic composition;
   a first pump fluidly coupled to the test cell and the first and second brine fluid tanks;
   an inert gas storage tank containing an inert gas, the inert gas storage tank fluidly connected to the test cell;
   a back pressure regulator configured for controlling a pressure of the inert gas in the test cell;
   a control system communicably coupled to the pump;
   a hydrocarbon fluid tank containing the hydrocarbon fluid, the hydrocarbon fluid tank fluidly connected to the test cell; and
   a second pump fluidly connected to the hydrocarbon fluid tank and the inert gas storage tank, the second pump is configured to pump the hydrocarbon fluid and the inert gas into the test cell.

2. The system of claim 1, further comprising the control system being communicably coupled to one or more valves.

3. The system of claim 1, further comprising a third brine fluid tank configured to hold a volume of a third brine fluid, the third brine fluid having a third initial ionic composition.

4. The system of claim 3, wherein the first pump is fluidly coupled to the test cell and the first, second, and third brine fluid tanks.

5. The system of claim 1, further comprising a drain line configured to drain the first brine fluid and hydrocarbon fluid from the test cell.

6. The system of claim 5, further comprising a filter configured to filter the drained first brine fluid and hydrocarbon fluid.

7. The system of claim 6, further comprising an ionic chromatography unit for measuring a ionic composition of the filtered brine fluid.

* * * * *